United States Patent [19]

Ream et al.

[11] Patent Number: 4,487,958

[45] Date of Patent: Dec. 11, 1984

[54] PROCESS FOR PREPARING A DIESTER OF OXALIC ACID

[75] Inventors: Bernard C. Ream, Charleston; Joseph P. Henry, S. Charleston; Louis A. Kapicak, Charleston, all of W. Va.

[73] Assignee: Union Carbide Corporation, Danbury, Conn.

[21] Appl. No.: 428,816

[22] Filed: Sep. 30, 1982

[51] Int. Cl.$^3$ .............................................. C07C 67/36
[52] U.S. Cl. ..................... 560/204; 502/162; 502/213; 502/262; 502/326; 502/327; 560/193
[58] Field of Search ............................. 560/204, 193; 252/466 R; 502/162, 213, 262, 326, 327

[56] References Cited

U.S. PATENT DOCUMENTS

| | | | |
|---|---|---|---|
| 4,138,587 | 2/1979 | Yamasaki et al. | 560/204 |
| 4,229,591 | 10/1980 | Nishimura et al. | 560/193 |
| 4,384,133 | 5/1983 | Miyazaki et al. | 560/204 |

Primary Examiner—Natalie Trousof
Assistant Examiner—Vera C. Clarke
Attorney, Agent, or Firm—Norman L. Balmer

[57] ABSTRACT

A process is disclosed for preparing a diester of oxalic acid by contacting carbon monoxide and an ester of nitrous acid in the vapor state under a pressure in the presence of a supported palladium monolith catalyst.

15 Claims, No Drawings

PROCESS FOR PREPARING A DIESTER OF OXALIC ACID

TECHNICAL FIELD

This invention relates to a novel process for preparing diesters of oxalic acid. More particularly, this invention relates to a process for preparing a diester of oxalic acid which comprises contacting carbon monoxide with an ester of nitrous acid under pressure in the presence of a palladium monolithic catalyst.

BACKGROUND OF THE INVENTION

The preparation of diesters of oxalic acid (oxalates) is of particular interest to the chemical industry owing to the varied uses of these compounds. Not only may these diesters serve to act as the starting materials for such important compounds as oxalic acid, oxamide or ethylene glycol but they may also find extensive use as intermediates for dyes, pharmaceuticals, and the like.

Prior to the instant invention, there have been proposed numerous processes for the preparation of diesters of oxalic acid employing various catalysts, cocatalysts, reaction accelerators, and the like, for use in a liquid phase reaction to make oxalates. However, these conventional processes suffer from significant by-product formation as would be expected from the conventional liquid phase processes.

A particularly interesting attempt to prepare diesters of oxalic acid in the liquid phase is disclosed in U.S. Pat. No. 4,138,587. This patent employs nitric acid or a nitrogen oxide as an accelerator in the presence of a solid platinum group metal or salt thereof, molecular oxygen, an alcohol and carbon monoxide to produce the diester of oxalic acid. Unfortunately, the process is a liquid phase process and suffers in several significant practical aspects, such as catalyst losses by virtue of solvation, dissolution, large by-product formation, low efficiencies to product, to name a few.

U.S. Pat. No. 4,229,591 discloses a vapor phase process. The process disclosed in the patent involves contacting an ester of nitrous acid with carbon monoxide in the gaseous phase under normal pressure in the presence of a solid catalyst containing metallic palladium or a salt thereof at a temperature of 50° C. to 200° C., the ester of nitrous acid being a nitrous acid ester of an alcohol having 1 to 8 carbon atoms.

Although this above-described process is advantageous, as compared to liquid phase processes the process fails to distinguish the role played by the carrier for the catalysts employed in such a heterogeneous vapor phase process. This is better shown by reference to the examples of the patent (U.S. Pat. No. 4,229,591). Examples 1 to 24 depict various palladium catalysts but in each case the carrier for the palladium catalyst was either carbon or $SiO_2$. The specification also refers to alumina, diatomaceous earth, pumice, zeolite, and molecular sieves. Obviously, the broad general listing of carriers (supports) fails to signify any advantage of one carrier over another. For example, carbons and silica carriers ($SiO_2$) are carriers with high surface areas (much greater than 10 $m^2/g$). Further, the patent mentions "alumina" as a carrier, and this encompasses a wide variety of materials ranging from high surface area acidic aluminas (gamma-aluminas), fibrous alumina, to alpha-alumina.

DISCLOSURE OF THE INVENTION

The invention comprises a vapor phase, heterogeneous process for preparing a diester of oxalic acid which comprises contacting a vaporous alkyl ester of nitrous acid (an alkyl nitrite) with carbon monoxide in the vapor state in the presence of a solid supported palladium catalyst comprising metallic palladium or a salt thereof deposited on a monolithic carrier. The monolithic carrier is preferably a monolithic carrier having a washcoat and/or a monolithic carrier formed of an oxide such as an alumina, for example, alpha-alumina or gamma-alumina. The process provides for the manufacture of a dialkyl oxalate in which the alkyl moiety corresponds to the alcohol used in making the ester of nitrous acid. The use of a monolithic support for palladium provides a decrease in the rate of formation of by-products while the rate of formation of the diester of oxalic acid is maintained or increased.

DETAILED DESCRIPTION OF THE INVENTION

By employing a palladium catalyst deposited on a monolithic carrier, i.e., a monolithic support, in the vapor phase heterogeneous process for the manufacture of diesters of oxalic acid (i.e., oxalate process) from nitrous acid esters and carbon monoxide several advantages may be obtained, such as increased conversion of the nitrous acid ester, an increased rate to the diester product, longer catalyst life, less by-product formation, improved process conditions and a lower palladium content for the catalyst. (The terms "vapor state" and "vapor phase" are equivalent in their use herein.)

The esters of nitrous acid which are employed in the process may be formed by conventional synthetic schemes or may be provided in the form of a nitrogen compound which in situ may provide, by reaction with an alcohol, as described herein, an ester of nitrous acid in the reaction system.

Exemplary of nitrogen oxide compounds which can be used to make nitrous acid esters or can be employed to form the ester in situ are nitrogen monoxide, nitrogen dioxide, dinitrogen trioxide, dinitrogen tetroxide, and hydrates thereof. In the case where nitrogen monoxide is employed it is necessary to employ molecular oxygen therewith to form the requisite nitrogen compound.

The preferred esters of nitrous acid (also referred to as alkyl nitrites) are esters derived from saturated monohydric aliphatic alcohols to form alkyl nitrite, such as those formed from a saturated monohydric open-chain aliphatic alcohol having 1 to 8 carbon atoms or an alicyclic alcohol having 1 to 8 carbon atoms. The most preferred esters of nitrous acid are those prepared from methanol and ethanol. As the alcohol component may be mentioned aliphatic alcohols such as methanol, ethanol, n-propanol, isopropanol, n-butanol, isobutanol, sec-butanol, tert-butanol, n-amyl alcohol, isoamyl alcohol, hexanol, octanol, etc., and an alicyclic alcohol such as cyclohexanol, methylcyclohexanol, etc. These alcohols may contain therein a substituent such as an alkoxy group which does not inhibit the reaction.

The process by which the ester of nitrous acid is prepared is not narrowly critical so long as the ester of nitrous acid does not contain deleterious components, such as nitric acid, and nitrates which may adversely affect the palladium catalyst. A preferred and highly advantageous process for preparing the methyl and ethyl esters of nitrous acid is disclosed in co-pending U.S. Ser. Nos. 227,798, filed Jan. 23, 1981, now abandoned; and 239,761, filed Mar. 12, 1981, now U.S. Pat. No. 4,353,843, to Arthur Doumaux et al. wherein a novel vapor phase process for the preparation of methyl and ethyl nitrite is provided. The disclosure of these applications is incorporated by reference herein. An improved process is disclosed in U.S. Ser. No. 307,201, filed Sept. 30, 1981.

The aforementioned esters of nitrous acid are employed in the instant process in the vapor state reaction with carbon monoxide which may be obtained from any conventional source. It may be pure, contain small amounts of hydrogen, and/or it may be diluted with an inert gaseous diluent such as nitrogen, carbon dioxide and the like. The concentration of carbon monoxide, in the reaction zone is not narrowly critical and may vary over a wide range between about 1 and about 99 percent by volume. Typically, the concentration of carbon monoxide is in the range of between about 10 percent and about 95 percent by volume, wherein the actual concentration of carbon monoxide in the reaction mixture will depend on the alkyl nitrite employed and its concentration, the catalyst employed in the process, concentration of inert gaseous diluent and the selected process conditions.

It may be preferable to carry out the oxalate process in the presence of an inert gaseous diluent to moderate the reaction to preclude the formation of explosive gaseous mixtures and prevent the formation of excessive amounts of undesirable by-products. The inert gaseous diluent may be added with the alkyl nitrite, should it not have been employed in making the alkyl nitrite. As the inert diluent, it is preferred to employ nitrogen, carbon dioxide, or other inert gaseous compounds. The use of carbon dioxide may be preferred since it provides a higher heat capacity as compared to nitrogen. The inert gaseous diluent is employed in sufficient amount to provide the aforementioned objectives. The inert gaseous diluent may be employed in the process such that between about 0 (zero) and about 99 percent by volume of the reaction volume comprises inert gaseous diluent. Typically, the concentration of inert gaseous diluent is between about 1 percent and about 90 percent by volume wherein the actual concentration employed is chosen based on the process parameters, as before discussed with respect to the concentration of carbon monoxide.

The oxalate process is generally carried out at a temperature between about 50° C. and about 200° C. and preferably between about 75° C. and about 160° C.

The reaction pressure is generally atmospheric (14.7 psia) or superatmospheric pressure, such that the pressure is between about 1 atmosphere (14.7 psia) and about 15 atmospheres and most preferably between about 1 atmosphere and about 7 atmospheres. If desired, subatmospheric pressure may be employed, although such is not preferred.

The vapor state reaction for the formation of the diesters of oxalic acid is preferably carried out by providing an oxalate forming reaction zone which is without deleterious amounts of water. While some amount of water may be tolerated in the reaction zone, the amount of water formed in the alkyl nitrite forming reaction zone is a deleterious amount and a sufficient amount of said water is removed therefrom prior to introduction to the oxalate forming reaction zone. This may be accomplished by use of a water condenser (such as a vapor-liquid separator) after alkyl nitrite formation or by the use of some other dehydration process. The amount of water which is deleterious to the vapor state reaction for the formation of diesters of oxalic acid is determined, in part, by the selection of ester of nitrous acid, temperature, pressure, etc. In general, a deleterious amount of water is that amount of water which causes a significant change in the rate of oxalate formed, causes a decrease in the efficiency of the process to oxalate product, or increases the production of by-products, as compared to the rate when a non-deleterious amount is present. In general, to prevent the presence of a deleterious amount of water the amount of water in the oxalate forming reaction zone is preferably less than about 5.0 percent by volume, based on the total reaction volume, more preferably less than about 2.0 percent by volume and most preferably less than about 0.5 percent by volume.

The process is preferably carried out in a tubular reactor with fixed catalyst. The monolith catalyst, as hereinafter described, may be pure palladium, i.e., a palladium metal monolith, or comprised of other inert materials, to enhance control over the reaction temperature.

The contact or residence time during which the process occurs is generally less than about 30 seconds, preferably between about 0.05 and about 10 seconds although longer or shorter residence times may be employed. Although the exact nature of the monolith catalyst which provides the improved product distribution is not completely understood, it is believed that the unique diffusion characteristics and decrease in the pressure drop through the catalyst bed, as compared to particulate catalysts, is at least in part involved in the observed decrease in the impurities formed in the process. Further, the form of the monolith provides for the use of a higher flow through the catalyst bed with the corresponding improved control of the heat generated by the exothermic reaction of the instant process.

CATALYST

In general terms, the special catalysts employed in this process comprise metallic palladium or salts thereof deposited on a monolithic carrier, including a palladium metal monolith. In addition a co-catalyst may be provided to enhance the life of the catalyst or provide other beneficial effects, such as increased production of the oxalate product. In any event metallic palladium or a salt thereof will be present on or as a part of the monolithic carrier. The term "monolith" or "monolithic" carrier is employed in its common meaning and refers to carriers which are continuous, unitary structures characterized by the presence of a plurality of relatively small substantially parallel fluid-flow passages. The passages may have any of a number of cell geometries such as circular, hexagonal, square, triangular, sinusoidal, and the like, such that a cross section taken perpendicular to the direction of fluid-flow represents a repeating pattern that can be described as a corrugated, lattice or honeycomb type structure. Representative of the monolithic carriers employable herein are those disclosed in U.S. Pat. No. 4,316,823 and U.S. Pat. No. 4,335,023, incorporated herein by reference thereto.

The monolithic carrier may be produced from or coated with conventional, porous, refractory materials which are essentially inert to the process reactants and products at reaction conditions yet which may enhance the overall characteristics of the monolithic carrier.

A preferred class of materials which may be used for coating a monolithic carrier prior to addition thereto of the palladium catalyst are generally labelled as "macroporous" materials and consist of porous materials having a low surface area of less than about 10 square meters per gram of carrier and preferably less than about 5 square meters per gram. The surface area is measured by the conventional B.E.T. method described by Brunauer, S., Emmet, P., and Teller, E., in J. Am. Chem. Soc. Vol. 60, pp 309–16, (1938), which method is incorporated herein by reference thereto. The palladium metal or salt thereof is subsequently applied to the coated monolithic carrier. The use of a particulate catalyst comprising a non-acidic low surface area particulate carrier for palladium metal or a salt thereof is disclosed in copending U.S. Ser. Nos. 227,640, now abandoned, and 239,762 filed Jan. 23, 1981 and Mar. 12, 1981, respectively.

The term "low surface area" is used herein to characterize a monolith which has or which is coated with a material, such as an alpha-alumina, such that the monolith has a surface area of no more than about 10 square meters per gram, preferably in the range of from about 0.0001 to about 10 square meters per gram, and most preferably from about 0.01 to about 5 square meters per gram.

Typical of materials which may be employed as a coating on or in forming the monolith carrier are an alumina (e.g., an alpha-alumina or a gamma-alumina), silicon carbide, and zirconia and the like. The monolith is preferably formed of or coated with an aggregate of alumina particles, which may be fused together or cemented together with, for example, silica or baryta such that the monolith is at least 70 percent by weight alumina particles.

In most cases the preferred monolithic carrier will likely be a monolithic carrier formed of or coated with alpha-alumina, such as described in the patent literature: see for example, U.S. Pat. Nos. 2,294,383; 3,172,893; 3,332,887; 3,423,328; and 3,563,914, incorporated herein by reference thereto.

The metallic palladium or salt thereof that is deposited on the carrier is typically in the form of small particles. The particle size of the deposited metallic palladium or salt thereof and the relative dispersion of the particles appear to be important in the performance of the monolith catalyst. The greater the dispersion, generally, it is believed the more the production rate is enhanced. The actual dispersion of the particles on the monolith carrier is believed to be related to the unique characteristics provided by the monolith carrier.

The palladium or salt thereof may be provided to the monolith carrier (or on a coated monolith carrier) by a number of techniques, but the two techniques which are frequently employed involve, in one case, the impregnation of the monolith carrier with a palladium solution followed by heat treatment of the impregnated monolith carrier to effect deposition of the palladium on the monolith carrier and, in the other case, the coating of the palladium on the support by the preformation of palladium into a slurry such that the palladium particles are deposited on the carrier and adhere to the surface of the monolith when the monolith is heated to remove the liquids present. These various procedures are exemplified in various U.S. Pat. Nos. such as 2,773,844; 3,207,700; 3,501,407; 3,664,970 (see British Pat. No. 754,593); and 3,172,893, which are incorporated herein by reference thereto.

CARRIER SELECTION

The chemical composition of the monolith carrier is not narrowly critical. The most preferred monolith carrier is a monolith carrier with washcoat of an oxide, e.g., an alpha-alumina or a gamma-alumina. The general chemical and physical properties of the monolith carrier are hereinafter discussed.

In general, the microstructure of the monolithic carrier is relevant in defining the physical properties of the monolithic carrier. The arrangement and size of the crystalline and glass phases, the pore structure, and the chemical composition serve to determine such physical properties as thermal expansion, thermal conductivity, strength, melting point, surface area, and the like. The microstructure of the final product generally depends on the raw materials, fabrication techniques, sintering temperature, time and the like. The manufacture of such monolithic carriers is well known in the art.

Even though the chemical composition of a given monolith is described as being of a particular material (e.g., cordierite, $2MgO:2Al_2O_3:SiO_2$) the monolith generally exists as one or more phases. The secondary phase depends on the raw materials, the impurities present therein and the method used in manufacturing.

The porosity of a given monolithic carrier may be controlled in large part by the methods of fabrication, starting material and the final sintering time and temperature. In many instances a starting material that will burn out during sintering is added to a monolith formulation to increase the porosity of the final monolith product.

Along with the composition and geometrical shape of the monolith, the nature and amount of wall porosity may have an influence on the monolith's physical properties and on its use in the instant process. General physical properties such as density, thermal conductivity, and washcoat adhesion are influenced by the amount, shape, and size distribution of the wall porosity. Although traditional ceramic materials are designed to have low porosity, a monolith's wall generally has 30–40 percent open porosity. The wall porosity and the size distribution of the pores can be modified by changing the processing techniques.

In general, the larger the volume of the macropores on the surface of the monolith, the greater ability of the monolith to pick up the palladium catalyst during impregnation. The most widely used method of depositing the catalyst on the monolithic carrier consists of first coating the monolith with a washcoat material (usually an oxide) and then depositing on this washcoat layer the metal catalyst. The use of a washcoat on the monolith carrier is not required in the instant process but if preferred, especially when the monolith carrier comprises a metal monolith (except when it is a palladium metal monolith) or a material which may exhibit some reactivity under reaction conditions. Most monoliths employed in the instant process can be made directly with suitable surface areas or the monoliths may then be coated in a variety of ways with 5–20 wt% of high surface area (10–200 $m^2$/gram) oxides or a low surface area oxide (0.001 to less than 10 $m^2$/gram).

The surface area of the monolith per total weight is relatively low when compared with particulate supports, but with washcoated monoliths in which pore diffusion may be rate controlling, it is desirable to have the metal on the external surface. For coated monolithic catalysts the primary support surface area of interest is the area per gram of washcoat because this will determine the catalytic utilization of the metal catalyst.

Three common methods, among others, are commonly employed for making a monolith carrier with a washcoat on the monolithic structure. A powder slurry of an oxide can be made in which oxide the monolith is dipped therein. A second method involves dipping the monolith into a salt solution containing the desired metal catalyst ion and then heating the system to decompose the salt and form the oxide. A third method involves contacting the support with the desired organic and inorganic metal salt and then contacting this system with a precipitating agent to produce a solid, for example, the hydroxide, which is subsequently heated to give the monolith the desired oxide coating. The manner, i.e., method, in which the washcoat is formed on the monolith may affect the physical properties of the resultant monolith carrier although the extent of such effects in the instant process is not clearly understood at this time.

Among the properties which a washcoated monolith desirably possesses are uniformity, desired surface area, adherency to the monolith, and high temperature stability. The first three properties have been discussed or are self explanatory but, in addition, the monolith carrier must be thermally stable at the temperature of the process. At the relatively low temperatures employed in the instant process the thermal stability of the monolith is not generally a concern. Further, best utilization of the palladium metal is obtained when the monolith's washcoat cannot lose much of its surface area under process conditions.

The above described procedures are generally useful for preparing monolith carriers. Commercially, a procedure disclosed by Keith et al. in U.S. Pat. No. 3,565,830 (1971) may be employed and U.S. Pat. No. 3,565,830 is incorporated herein by reference thereto. This patent discusses the method of preparing a monolith carrier, washcoat for a monolith carrier from hydrous aluminas, the method for applying the washcoat, the preparation of the catalyst solutions, and subsequent impregnations, precipitations and calcinations. In addition, it discloses the importance of monolith porosity to washcoat and catalyst attachment.

When it is desired to provide the monolith with an alumina washcoat a colloidal suspension of alumina can be used to produce the washcoat. Such a colloidal suspension can be prepared using any of the commercially available aluminas. In practice an alumina powder is added to the water and the pH adjusted to approximately 3. The suspension is boiled and stirred for several hours producing an alumina gel. This gel is used to coat the monolith. The amount of alumina deposited on the monolith is related to the boiling time and the viscosity, which, in turn, is related to the weight of solids employed in making the alumina gel.

A monolith carrier having relatively small amounts of a washcoat of a high surface area alumina (e.g., a gamma alumina) may be made by using a solution of aluminum nitrate; this solution would strip away much of the excess material after the monolith has been dipped. Such a dipping process can be repeated several times with intermittent drying steps and a final firing at 500° or 600° C. to provide a monolith with a washcoat having a desired loading and surface area.

Another technique widely used to coat monolithic carriers is a variation of the above mentioned procedure wherein the monolith is contacted with an organic or inorganic metal salt, the salt is precipitated in situ and the monolith is heated to develop the oxide washcoat.

The preceding paragraphs describe general methods of forming a monolith and for providing a washcoat on a monolith. After the monolith has been washcoated, when desired, the next step in producing a catalyst is the deposition of the active material (i.e., catalyst), in this case palladium, with a procedure similar to those used when pelleted catalysts are employed. A detailed description of noble metal deposition on coated monoliths is disclosed in German Pat. Nos. 2,317,560 (1973) and 2,317,536 (1973).

It is believed that the dispersion of the metal catalyst on the monolith carrier is quite different from that observed with particulate carriers with a greater degree of dispersion being present when the monolith carrier is employed. This increased dispersion of the metal catalyst may, in part, account for the results obtained when the monolith carriers are employed in the instant process.

The palladium solution used to impregnate the carrier generally comprises a palladium salt or complex in a solvent or complexing/solubilizing agent. The particular palladium salt or complex employed is not critical and may be chosen, for example, from among palladium nitrates, sulfates, halides, phosphates, carboxylates (such as palladium acetate, benzoate, oxalate, citrate, phthalate, lactate, propionate, butyrate and higher fatty acid salts), palladium acetylacetonate, and the like. Although any palladium salt may be used to prepare the palladium catalyst employed in the process of this invention the catalyst is preferably prepared such that the catalyst is substantially free of halogen, especially chloride, and sulfur. The presence of such halogen or sulfur atoms may interfere with the formation of the diester of oxalic acid. In addition, the presence of halogen or sulfur atoms may result in increased production of deleterious by-products such as carbonates, formate and the like with the resulting loss in yield of the oxalic acid diester. Thus, the concentration of halogen or sulfur atom is preferably less than about 10 ppm, by weight, based on the amount of palladium deposited on the monolithic carrier.

The amount of palladium deposited on the carrier is not narrowly critical and is in the range of from about 0.001 to about 10 percent by weight, preferably from about 0.01 to about 5 percent by weight and most preferably from about 0.1 to about 2 percent by weight, calculated as metallic palladium.

The particle size of palladium metal or salt thereof deposited upon the monolithic carrier and the dispersion of the palladium on the monolithic carrier are a function of the catalyst preparation procedure employed. Thus, the particular choice of solvent and/or complexing agent, palladium salt, heat treatment conditions and catalyst carrier may affect, to varying degrees, the size of the resulting palladium particle. For monolithic carriers of general interest for the production of diesters of oxalic acid, it is believed that a distribution of palladium particle sizes below about 10,000 Angstroms is preferred. However, the role of particle size and dispersion of the palladium upon the effectiveness of the catalyst in making the diesters of oxalic acid is not clearly understood. In view of the fact that the palladium particles may migrate on the surface of the catalyst when used in a catalytic reaction, resulting in a marked change in their size and shape, palladium particle size may or may not be a significant factor in affecting catalytic performance, although such migration is not believed to occur under process conditions. A high dispersion of palladium is considered to be preferred.

EXPERIMENTAL PROCEDURE

The following examples were carried out in a tubular reactor formed of a 4 foot long by 1 inch (inside diameter) stainless steel tube and operated in a down-flow configuration. The top (inlet) of the reactor was packed with glass beads to act as a preheating zone for the mixture of alkyl nitrite, inert gaseous diluent and carbon monoxide prior to introduction to the catalyst bed. The catalyst bed was formed of 10 cc of a supported palladium catalyst (as designated in each example) held in place by a thin porous glass wool plug. The tubular reactor was within a liquid containing jacket which was wrapped with electrical resistance heaters to provide even heating. The temperature of the catalyst bed was measured by a thermocouple placed therein. The alkyl nitrite was introduced by passing a $CO/N_2$ mixture through liquid alkyl nitrite (saturator) to provide a gaseous stream with CO, $N_2$ and alkyl nitrite in the vapor state. The reaction product was analyzed by vapor phase chromatography.

EXAMPLES 1 AND 2

Examples 1 and 2 were carried out according to the above-described Experimental Procedure. Example 1 is an example carried out in accordance with this invention and example 2 is a comparative example.

The temperature, pressure, reaction time, ratio of carbon monoxide to alkyl nitrite (ethyl nitrite was employed) and weight percent alkyl nitrite in the feed are set forth in Table I, hereinafter. The supported palladium catalyst employed in example 1 was a palladium monolith catalyst from Engelhard Industries Division, Engelhard Minerals and Chemicals Corporation, Newark, N.J., comprising 0.61 percent by weight palladium (12.5 mg of palladium) on a gamma-alumina washcoated ceramic monolith (Lot No. 7039-1) having a surface area of about 8.0 square meters per gram. The cell geometry was square with 1 millimeter sides and the length of the monolith in the direction of fluid-flow as one (1) inch. The catalyst employed in example 2 was a supported palladium catalyst comprising 0.5 percent by weight palladium (48.4 mg of palladium) on gamma alumina (Lot No. 29064) from Engelhard formed in ⅛ inch cylinders.

The results set forth in Table I show that the use of the monolith catalyst under comparable process conditions resulted in an increase in the rate to the oxalate product, the conversion of reactant to oxalate product (based on alkyl nitrite) and an increase in weight percent alkyl nitrite converted.

TABLE I

| Example | EtONO[1] | Temp.[2] | Press[3] | Time[4] | EtONO (%)[5] | Rate[6] | | | | Efficiency[7] | | | | Conv[8] |
| --- | --- | --- | --- | --- | --- | --- | --- | --- | --- | --- | --- | --- | --- | --- |
| | | | | | | DEO | DEC | EF | ACH | DEO | DEC | EF | ACH | |
| 1 | 3.9 | 110.5 | 6.2 | 1.4 | 7.0 | 3.82 | 0.22 | 0.27 | 0.23 | 90.0 | 4.7 | 2.9 | 2.4 | 95.5 |
| 2 | 3.9 | 109.0 | 6.2 | 1.4 | 7.0 | 2.72 | 0.28 | 0.21 | 0.24 | 84.4 | 9.4 | 3.1 | 3.1 | 86.1 |

[1] molar ratio of carbon monoxide to ethyl nitrite
[2] temperature in degrees centigrade
[3] pressure in pounds per square inch gauge
[4] residence time in seconds
[5] volume percent ethyl nitrite in the feed
[6] rate in gram-moles per liter per hour for: DEO = diethyl oxalate; DEC = diethyl carbonate; EF = ethyl formate; ACH = acetaldehyde
[7] efficiency based on ethyl nitrite for; DEO = diethyl oxalate; DEC = diethyl carbonate; EF = ethyl formate; ACH = ethyl acetaldehyde
[8] conversion based on ethyl nitrite

What is claimed is:

1. The vapor phase heterogeneous process for preparing a diester of oxalic acid which comprises contacting a vaporous ester of nitrous acid with carbon monoxide in the vapor state, in the presence of a solid supported palladium monolith catalyst comprising metallic palladium or a salt thereof deposited on a monolithic carrier at a temperature of between about 50° C. and about 200° C., and recovering a diester of oxalic acid, in which the ester group corresponds to the alcohol used in making the ester of nitrous acid.

2. The process of claim 1 wherein the monolith carrier has a washcoat comprising a gamma alumina.

3. The process of claim 1 wherein the process is carried out at a pressure of from about atmospheric to superatmospheric pressure.

4. The process of claim 3 wherein the pressure is between 1 atmosphere and about 15 atmospheres.

5. The process of claim 4 wherein the pressure is between about 1 atmosphere and about 7 atomspheres.

6. The process of claim 1 wherein the ester of nitrous acid is methyl nitrite.

7. The process of claim 1 wherein the ester of nitrous acid is ethyl nitrite.

8. The process of claim 1 wherein between about 0.1 and about 2 percent by weight palladium on said supported palladium catalyst is employed.

9. The process of claim 1 wherein from about 0.2 to about 1.2 percent by weight palladium is present.

10. The process of claim 1 wherein the supported palladium catalyst is substantially free of sulfur atoms.

11. The process of claim 1 wherein the palladium supported catalyst is substantially free of halogen atoms.

12. The process of claim 1 wherein the palladium particle size is less than 10,000 Angstroms.

13. The process of claim 1 wherein the monolith carrier has a washcoat comprising an alpha alumina.

14. The process of claim 1 wherein the monolithic carrier comprises a coated monolithic carrier in which the coating comprises a porous, refractory material.

15. The process of claim 14 wherein the coating comprises alumina.

* * * * *